United States Patent
Liang et al.

(10) Patent No.: US 9,751,896 B1
(45) Date of Patent: Sep. 5, 2017

(54) ASYMMETRIC 7-N ISATIN DIMER SCHIFF BASE COMPOUNDS WITH ANTITUMOR ACTIVITIES AND A METHOD OF PREPARING THE SAME

(71) Applicants: Chengyuan Liang, Xi'an (CN); Minyi Jia, Xi'an (CN); Danni Tian, Xi'an (CN); Xuechuan Wang, Xi'an (CN); Xuefeng Chen, Xi'an (CN); Juan Li, Xi'an (CN); Guang Tong, Xi'an (CN)

(72) Inventors: Chengyuan Liang, Xi'an (CN); Minyi Jia, Xi'an (CN); Danni Tian, Xi'an (CN); Xuechuan Wang, Xi'an (CN); Xuefeng Chen, Xi'an (CN); Juan Li, Xi'an (CN); Guang Tong, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 15/489,706

(22) Filed: Apr. 17, 2017

(30) Foreign Application Priority Data

Sep. 30, 2016 (CN) .......................... 2016 1 0871776

(51) Int. Cl.
*C07D 401/02* (2006.01)
*C07D 401/10* (2006.01)
*C07D 401/14* (2006.01)
*A61K 31/437* (2006.01)
*A61K 31/4353* (2006.01)
*C07D 519/00* (2006.01)

(52) U.S. Cl.
CPC .................................. *C07D 519/00* (2013.01)

(58) Field of Classification Search
CPC .. C07D 401/02; C07D 401/10; C07D 401/14; A61K 31/437; A61K 31/4353
USPC .......................... 546/119, 121; 514/300, 303
See application file for complete search history.

(56) References Cited

U.S. PATENT DOCUMENTS 7,314,887 B2 *  1/2008  Chen ..................... C07D 209/40
                                                                514/418

\* cited by examiner

*Primary Examiner* — Niloofar Rahmani

(57) ABSTRACT

A compound with antitumor activities is represented by formula:

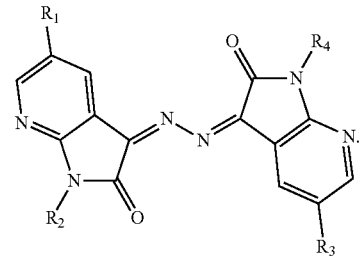

$R_1$, $R_2$, $R_3$, and $R_4$ are independently hydrogen, nitro, alkoxy, halogen, unsubstituted or substituted phenyl, or unsubstituted or substituted alkyl or cycloalkyl.

11 Claims, No Drawings

ASYMMETRIC 7-N ISATIN DIMER SCHIFF BASE COMPOUNDS WITH ANTITUMOR ACTIVITIES AND A METHOD OF PREPARING THE SAME

The present invention claims priority to Chinese Patent Application No. 201610871776.X, filed on Sep. 30, 2016, which is incorporated by reference for all purposes as if fully set forth herein.

BACKGROUND OF THE INVENTION

Field of the Invention

The present invention relates to the field of pharmaceutical chemistry, and more particularly, to asymmetric 7-N isatin dimer Schiff base compounds with antitumor activities and a method of preparing the same.

Discussion of the Related Art

Schiff bases have unique structural characteristics, i.e., N atom in the core structure has a lone pair of electrons. The lone pair of electrons make Schiff bases common ligands in coordination chemistry. Schiff bases can have two different groups that can react with various groups to obtain different derivatives, and can be used widely in chemical and biological applications. Asymmetric bis-Schiff base compounds, due to the asymmetric structure, have some special uses, for example, oxygen carriers, catalysts, insecticides, bacteriostatic agents, biological simulation process analog molecules. The synthesis and characterization of these compounds has also become an active subject in the chemical field.

Isatin and its derivatives (including N-isatin) have unique electronic properties and biological activities. Isatin can be synthesized in large industrial scale, and is relatively inexpensive raw materials. Many chemical reactions can be occurred at the 1, 2, and 3 positions and benzene ring of isatin, and isatin derivatives can be synthesized via different reactions.

The Schiff bases containing O, S, N atoms and its metal complexes have some antibacterial and antiviral activities. Isatin and its derivatives (including N-isatin) have some antibacterial, antiviral and neuroprotective activity. Herein, the inventors use 7-N isatin and its derivatives and hydrazine hydrate as starting materials to design and synthesize novel asymmetric 7-N isatin dimer Schiff base compounds.

SUMMARY OF THE INVENTION

In one embodiment, the present invention provides a compound with antitumor activities represented by formula I:

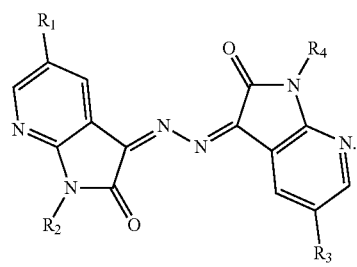

In formula I, $R_1$, $R_2$, $R_3$, and $R_4$ are independently hydrogen, nitro, alkoxy, halogen, unsubstituted or substituted phenyl, substituted or substituted benzyl, unsubstituted or substituted alkyl, or unsubstituted or substituted cycloalkyl.

In another embodiment, $R_1$ is hydrogen, methoxy, nitro, halogen, unsubstituted or substituted alkyl, or unsubstituted or substituted cycloalkyl; $R_2$ is hydrogen, unsubstituted or substituted alkyl, or unsubstituted or substituted cycloalkyl; $R_3$ is hydrogen, methoxy, nitro, halogen, unsubstituted or substituted phenyl, or unsubstituted or substituted alkyl or cycloalkyl; and $R_4$ is hydrogen, methyl, unsubstituted or substituted phenyl, unsubstituted or substituted benzyl, unsubstituted or substituted alkyl, or unsubstituted or substituted cycloalkyl.

In another embodiment, the compound is

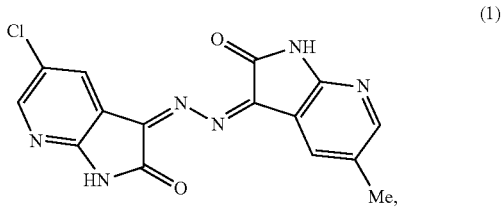

(1)

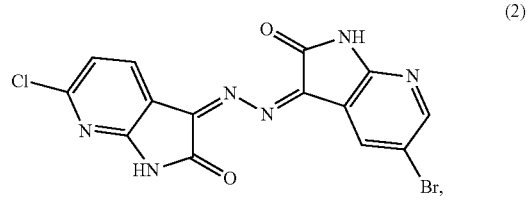

(2)

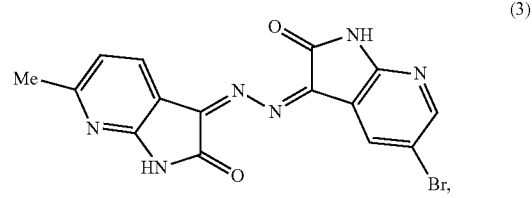

(3)

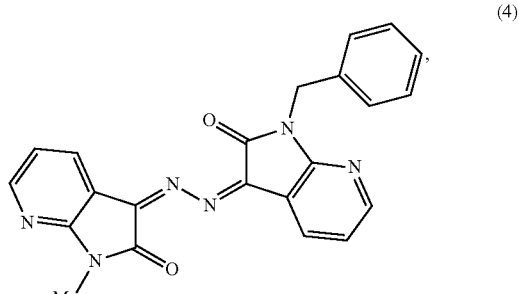

(4)

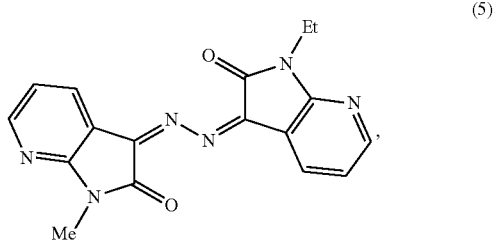

(5)

-continued

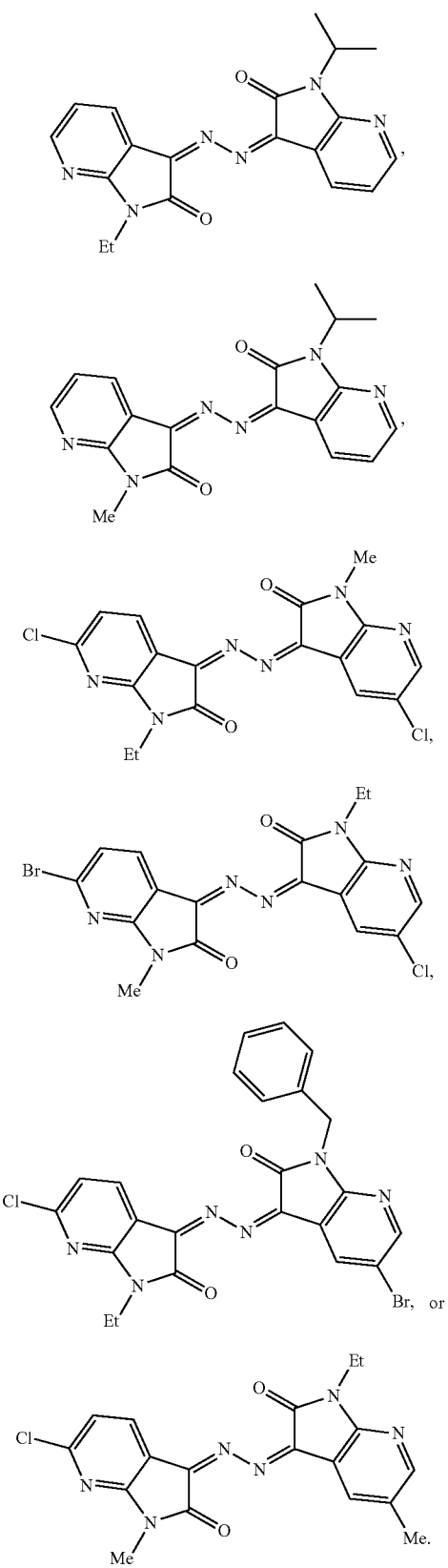

In yet another embodiment, the present invention provides a method of preparing the compounds described above. The method includes: reacting a compound of formula II with hydrazine hydrate ($N_2H_4 \cdot H_2O$) in an organic solvent to obtain a compound of formula III, and reacting the compound of formula III with a compound of formula IV in the organic solvent to obtain the compound of formula I,

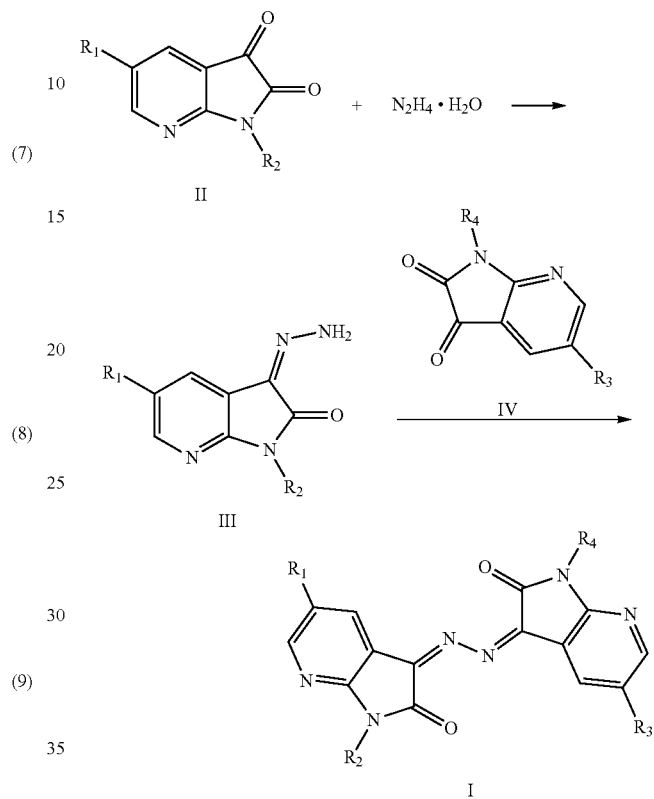

In another embodiment, the organic solvent is methanol, ethanol, or isopropanol.

In another embodiment, the compound of formula II and hydrazine hydrate ($N_2H_4 \cdot H_2O$) are heated in the organic solvent to 60-100° C. for 4 to 9 hours.

In another embodiment, the compound of formula III and the compound of formula IV are heated in the organic solvent to 60-100° C. for 2 to 6 hours.

In another embodiment, the method further includes recrystallizing the compound of formula I in methanol, ethanol, or isopropanol.

In another embodiment, a molar ratio of the compound of formula II and hydrazine hydrate ($N_2H_4 \cdot H_2O$) is 1:1 to 1:2.5.

In another embodiment, the molar ratio of the compound of formula II and hydrazine hydrate ($N_2H_4 \cdot H_2O$) is 1:1.5 to 1:2.

In another embodiment, a molar ratio of the compound of formula III and the compound of formula IV is 1:1 to 1:1.5.

In yet another embodiment, the present invention provides a method of using the compound in antitumor drug research, development, and application.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

Reference will now be made in detail to embodiments of the present invention.

As used herein, the term alkyl refers to a monovalent straight or branched chain, saturated aliphatic hydrocarbon radical having 1-8 carbon atoms. For example, alkyl refers to any of the hexyl alkyl and pentyl alkyl isomers as well as n-, iso-, sec- and t-butyl, n- and iso-propyl, ethyl, or methyl. The term cycloalkyl refers to any monocyclic ring of an alkane having 1-8 carbon atoms. For example, cycloalkyl refers to cyclopropyl, cyclobutyl, cyclopentyl, or cyclohexyl. The alkoxy refers to an alkyl ether group wherein the alkyl moiety is as defined above.

Alkyl, cycloalkyl, and alkoxy also include saturated aliphatic hydrocarbon radicals wherein one or more hydrogens are replaced with deuterium, for example, $CD_3$.

The term halogen refers to fluorine, chlorine, bromine and iodine. The term substituted phenyl refers to a phenyl substituted with 1-3 halogen, hydroxyl, nitro, alkyl, or alkoxy groups. The term substituted benzyl refers to a benzyl substituted with 1-3 halogen, hydroxyl, nitro, alkyl, or alkoxy groups.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Substituents include, for example, hydroxyl, halogen, amino, nitro, alkyl, and haloalkyl. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The present invention provides asymmetric 7-N isatin dimer Schiff base compounds with antitumor activities.

The structures of the asymmetric 7-N isatin dimer Schiff base compounds (hereafter, compounds) of the present invention are represented formula I:

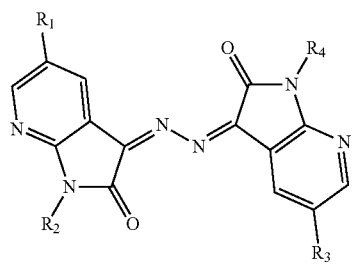

In formula I, $R_1$, $R_2$, $R_3$, and $R_4$ are independently hydrogen, nitro, alkoxy, halogen, unsubstituted or substituted phenyl, substituted or substituted benzyl, unsubstituted or substituted alkyl, or unsubstituted or substituted cycloalkyl.

Preferably, $R_1$ is hydrogen, methoxy, nitro, halogen, unsubstituted or substituted alkyl, or unsubstituted or substituted cycloalkyl.

Preferably, $R_2$ is hydrogen, unsubstituted or substituted alkyl, or unsubstituted or substituted cycloalkyl.

Preferably, $R_3$ is hydrogen, methoxy, nitro, halogen, unsubstituted or substituted phenyl, or unsubstituted or substituted alkyl or cycloalkyl.

Preferably, $R_4$ is hydrogen, methyl, unsubstituted or substituted phenyl, unsubstituted or substituted benzyl, unsubstituted or substituted alkyl, or unsubstituted or substituted cycloalkyl.

Preferably, the compounds have the following formulas.

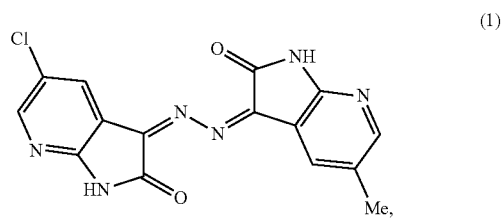
(1)

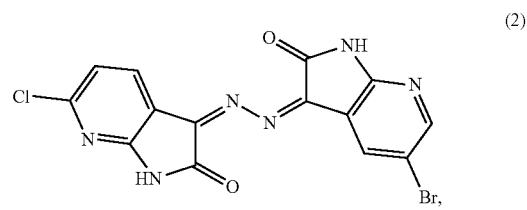
(2)

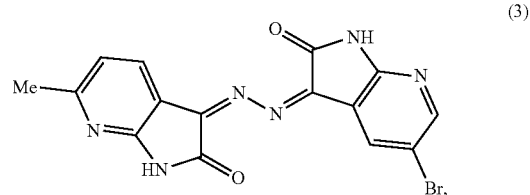 [SMILES: Cc1ccc2c(n1)NC(=O)/C2=N\N=C1/C(=O)Nc2ncc(Br)cc21]
(3)

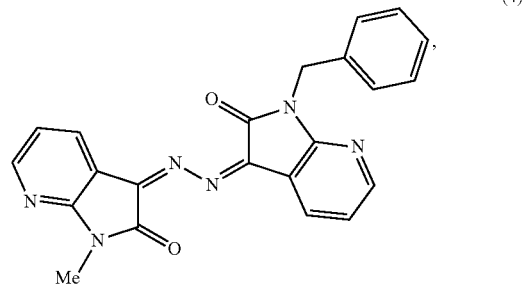
(4)

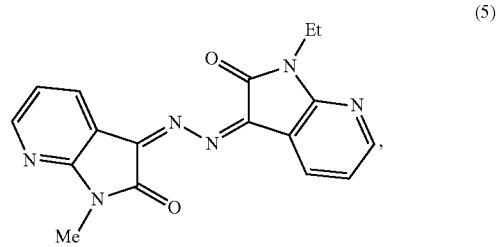 [SMILES: CCN1C(=O)/C(=N\N=C2/C(=O)N(C)c3ncccc32)c2cccnc21]
(5)

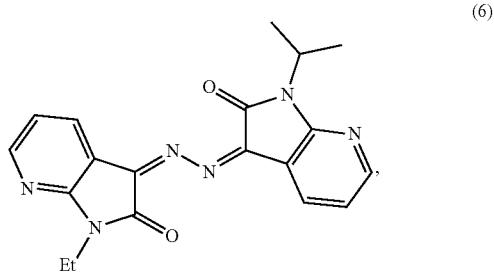
(6)

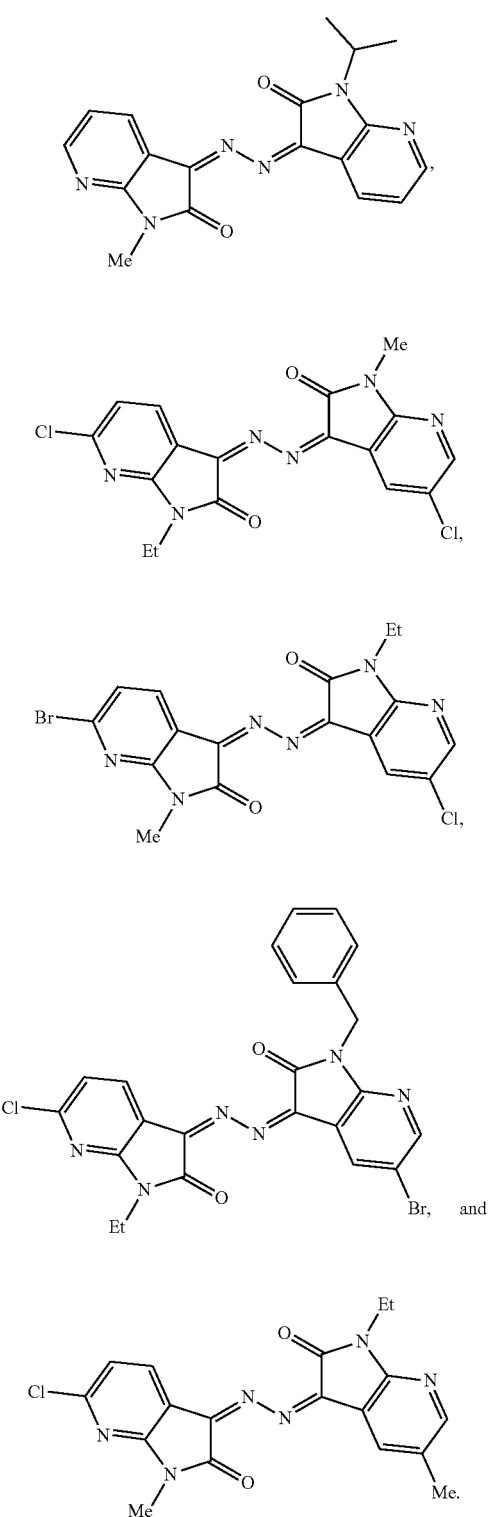

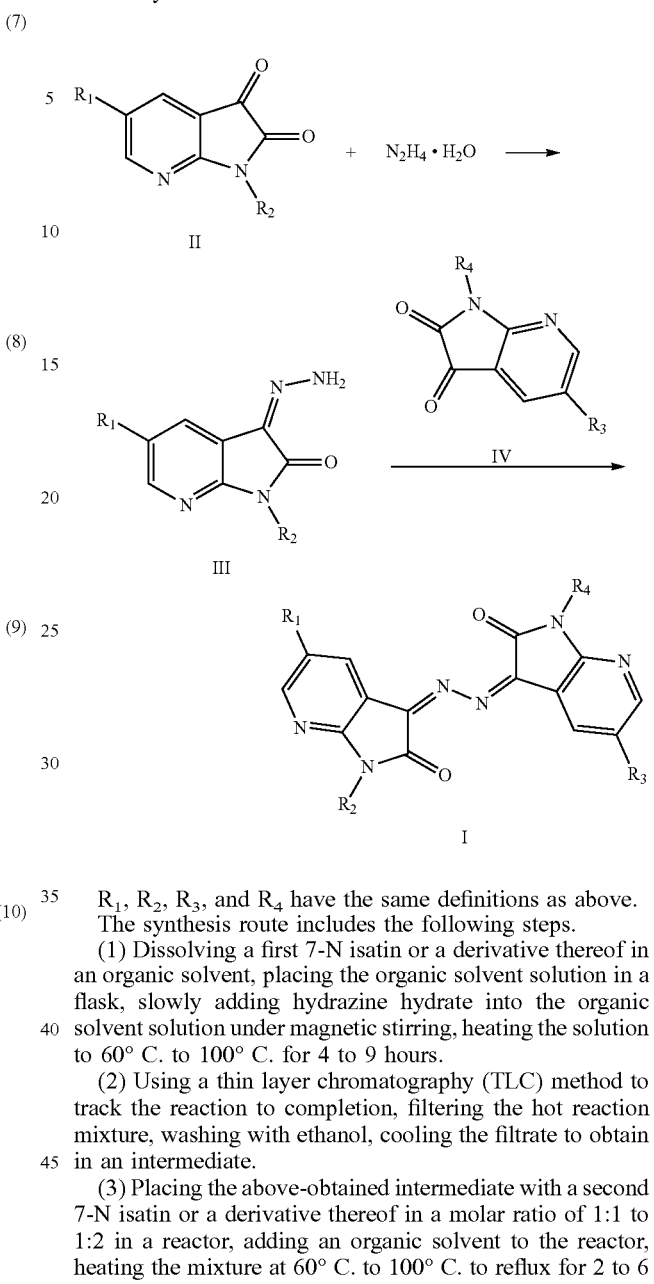

The synthetic route is as follows:

$R_1$, $R_2$, $R_3$, and $R_4$ have the same definitions as above.

The synthesis route includes the following steps.

(1) Dissolving a first 7-N isatin or a derivative thereof in an organic solvent, placing the organic solvent solution in a flask, slowly adding hydrazine hydrate into the organic solvent solution under magnetic stirring, heating the solution to 60° C. to 100° C. for 4 to 9 hours.

(2) Using a thin layer chromatography (TLC) method to track the reaction to completion, filtering the hot reaction mixture, washing with ethanol, cooling the filtrate to obtain an intermediate.

(3) Placing the above-obtained intermediate with a second 7-N isatin or a derivative thereof in a molar ratio of 1:1 to 1:2 in a reactor, adding an organic solvent to the reactor, heating the mixture at 60° C. to 100° C. to reflux for 2 to 6 hours.

(4) Tracking the reaction to completion using TLC, stopping heating, removing the condensing device, removing the solvent under reduced pressure, cooling the remaining mixture to room temperature, filtering the mixture, washing the filter cake with warm water to obtain crude product (an asymmetric 7-N isatin dimer Schiff base compound).

(5) Adding the crude product to an organic solvent in a reactor for recrystallization, and filtering and drying to obtain the target product.

The present invention also provides a method of preparing the above-described compounds.

The above-described compounds are obtained by reacting 7-N isatin (1H-pyrrolo[2,3-b]pyridine-2,3-dione) and its derivatives with hydrazine hydride in an organic solvent (e.g., ethanol) under heating and refluxing.

The organic solvent described in the above steps (1), (3) and (5) is methanol, ethanol, or isopropanol, and preferably ethanol.

The molar ratio of first 7-N isatin or a derivative thereof to hydrazine hydrate described in step (1) is 1:1 to 1:2.5, and preferably 1:1.5 to 1:2.

The reaction time described in the above step (1) is preferably 5 to 6 hours.

The reaction temperatures described in the above steps (1) and (3) are preferably 75° C. to 85° C.

The molar ratio of the intermediate of the above step (3) to second 7-N isatin or a derivative thereof is preferably from 1:1 to 1:1.5.

The reaction time described in the above step (3) is preferably 3 to 4 hours.

The advantages of the synthetic route are: inexpensive starting materials and environmental friendly, low production costs, mild reaction conditions and safe operation, suitable for industrial production.

INVENTIVE EXAMPLES

The invention will now be further elucidated with reference to specific embodiments. These examples are for illustrative purposes only and are not intended to limit the scope and spirit of the invention.

Example 1

The preparation of compound (1) (Z)-6-chloro-3-((Z)-(5-methyl-2-oxo-1H-pyrrolo[2,3-b]pyridin-3(2H)-ylidene)hydrazono)-1H-pyrrolo[3,2-b]pyridin-2(3H)-one is shown below.

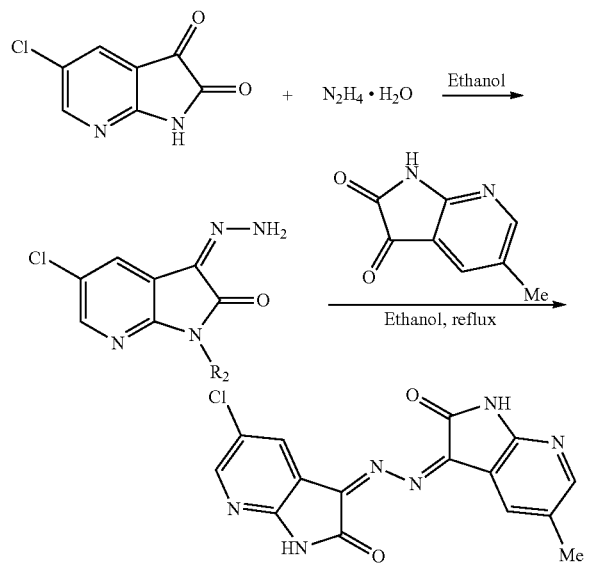

1.82 g (10 mmol) of 5-chloro-7-N isatin (5-chloro-1H-pyrrolo[2,3-b]pyridine-2,3-dione) was dissolved in 50 mL of ethanol and placed in a flask. The 5-chloro-7-N isatin ethanol solution was slowly added to 50 mL ethanol solution containing 0.75 g (15 mmol) of hydrazine hydrate under stirring. The mixture was heated to 80° C. for 6 hours. After TLC indicated that reaction was completed, the hot reaction mixture was filtered, and washed with ethanol. The filtrate was cooled and filtered to obtain an intermediate. The resulting intermediate was placed in a reactor with 1.62 g (10 mmol) of 5-methyl-7-N isatin (5-methyl-1H-pyrrolo[2,3-b]pyridine-2,3-dione), and 50 mL of ethanol was added to the reactor. The resulted mixture was heated to reflux at 80° C. under stirring for 6 hours. After TLC indicated that the reaction was completed, hearting was stopped and condensing device was removed. The reaction mixture was concentrated under reduced pressure, cooled to room temperature, and filtered. The filter cake was washed with warm water to obtain crude compound (1). Crude compound (1) was added to a reactor with 25 mL of ethanol for recrystallization. After filtration and drying, final product, light yellow crystalline powder (1.52 g), was obtained with an overall yield of 44.6%.

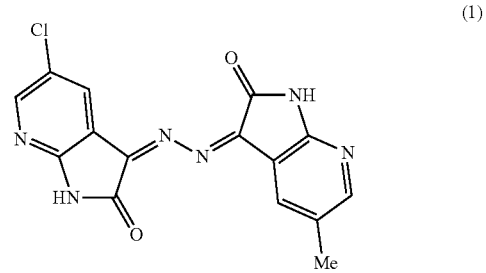

(1)

Compound (1) is light yellow crystalline powder. M.P. 174.5° C.; $^1$H-NMR (400 MHz, DMSO-d$_6$) δ(ppm): 8.13-8.42 (2H, m, J=1.5 Hz), 8.06 (2H, s), 7.95-8.03 (2H, m, J=1.5 Hz), 2.33 (3H, s); $^{13}$C-NMR (101 MHz, DMSOd$_6$) δ(ppm): 167.2, 161.0, 159.5, 158.8, 146.4, 140.9, 139.4, 138.2, 137.5, 136.6, 119.3, 118.6, 110.9, 18.1; MS (ESI) for (M+H)$^+$: 341.1.

Example 2

The preparation of compound (2) (Z)-3-((Z)-(5-bromo-2-oxo-1H-pyrrolo[2,3-b]pyridin-3(2H)-ylidene)hydrazono)-6-chloro-1H-pyrrolo[3,2-b]pyridin-2(3H)-one is shown below.

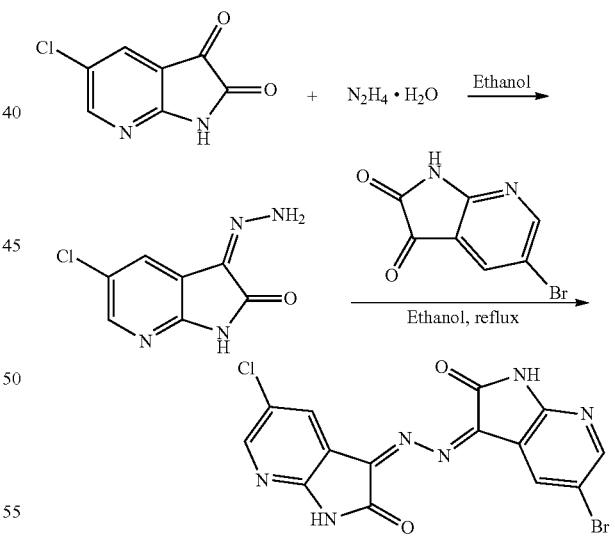

1.82 g (10 mmol) of 5-chloro-7-N isatin (5-chloro-1H-pyrrolo[2,3-b]pyridine-2,3-dione) was dissolved in 50 mL of ethanol and placed in a flask. The 5-chloro-7-N isatin ethanol solution was slowly added to 50 mL ethanol solution containing 0.75 g (15 mmol) of hydrazine hydrate under stirring. The mixture was heated to 80° C. for 6 hours. After TLC indicated that reaction was completed, the hot reaction mixture was filtered, and washed with ethanol. The filtrate was cooled and filtered to obtain an intermediate. The resulting intermediate was placed in a reactor with 2.26 g (10 mmol) of 5-bromo-7-N isatin (5-bromo-1H-pyrrolo[2,3-b]pyridine-2,3-dione), and 50 mL of ethanol was added to the reactor. The resulted mixture was heated to reflux at 80° C. under stirring for 6 hours. After TLC indicated that the reaction was completed, hearting was stopped and condensing device was removed. The reaction mixture was concentrated under reduced pressure, cooled to room temperature, and filtered. The filter cake was washed with warm water to obtain crude compound (2). Crude compound (2) was added to a reactor with 25 mL of ethanol for recrystallization. After filtration and drying, final product, yellow brown crystalline powder (3.11 g), was obtained with an overall yield of 76.9%.

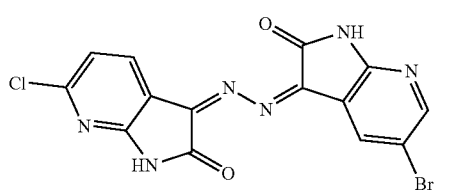

(2)

Compound (2) is yellow brown crystalline powder. M.P. 199.5° C.; $^1$H-NMR (400 MHz, DMSO-$d_6$) δ (ppm): 8.53 (1H, s, J=7.5 Hz), 8.32 (1H, d, J=7.5 Hz), 8.10 (1H, s, J=1.5 Hz), 8.06 (2H, s), 7.76 (1H, s, J=1.5 Hz); $^{13}$C-NMR (101 MHz, DMSO-d6) δ (ppm): 167.2, 160.9, 160.8, 155.4, 146.5, 141.3, 141.0, 139.4, 138.1, 137.5, 118.6, 112.9, 104.8; MS (ESI) for (M+H)$^+$: 406.9.

Example 3

The preparation of compound (3) (Z)-3-((Z)-(5-bromo-2-oxo-1H-pyrrolo[2,3-b]pyridin-3(2H)-ylidene)hydrazono)-6-methyl-1H-pyrrolo[3,2-b]pyridin-2(3H)-one is shown below.

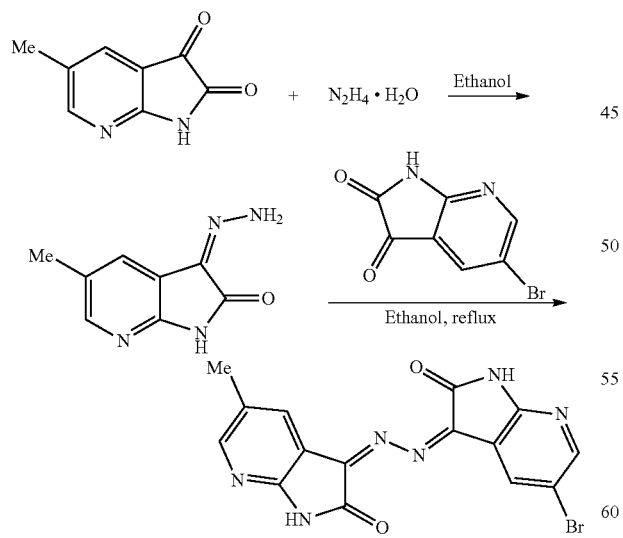

1.62 g (10 mmol) of 5-methyl-7-N isatin (5-methyl-1H-pyrrolo[2,3-b]pyridine-2,3-dione) was dissolved in 50 mL of ethanol and placed in a flask. The 5-methyl-7-N isatin ethanol solution was slowly added to 50 mL ethanol solution containing 0.75 g (15 mmol) of hydrazine hydrate under stirring. The mixture was heated to 80° C. for 6 hours. After TLC indicated that reaction was completed, the hot reaction mixture was filtered, and washed with ethanol. The filtrate was cooled and filtered to obtain an intermediate. The resulting intermediate was placed in a reactor with 2.26 g (10 mmol) of 5-bromo-7-N isatin (5-bromo-1H-pyrrolo[2,3-b]pyridine-2,3-dione), and 50 mL of ethanol was added to the reactor. The resulted mixture was heated to reflux at 80° C. under stirring for 6 hours. After TLC indicated that the reaction was completed, hearting was stopped and condensing device was removed. The reaction mixture was concentrated under reduced pressure, cooled to room temperature, and filtered. The filter cake was washed with warm water to obtain crude compound (3). Crude compound (3) was added to a reactor with 25 mL of ethanol for recrystallization. After filtration and drying, final product, reddish brown crystalline powder (2.75 g), was obtained with an overall yield of 71.6%.

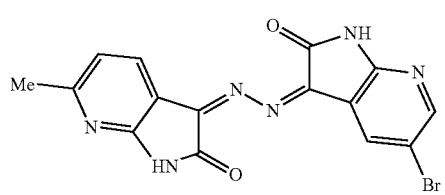

(3)

Compound (3) is reddish brown crystalline powder. M.P. 210.6° C.; $^1$H-NMR (400 MHz, DMSO-$d_6$) δ(ppm): 8.53 (1H, s, J=1.5 Hz), 8.23 (1H, s, J=1.5 Hz), 8.10 (1H, s, J=7.5 Hz), 8.02 (2H, s), 7.46 (1H, s, J=7.5 Hz), 2.33 (3H, s); $^{13}$C-NMR (101 MHz, DMSO-$d_6$) δ (ppm): 167.2, 161.0, 155.4, 144.9, 141.6, 141.1, 139.3, 138.5, 138.2, 116.8, 112.9, 104.7, 18.2; MS (ESI) for (M+H)$^+$: 385.0.

Example 4

The preparation of compound (4) (Z)-3-((Z)-(1-benzyl-2-oxo-1H-pyrrolo[2,3-b]pyridin-3(2H)-ylidene)hydrazono)-1-methyl-1H-pyrrolo[3,2-b]pyridin-2(3H)-one is shown below.

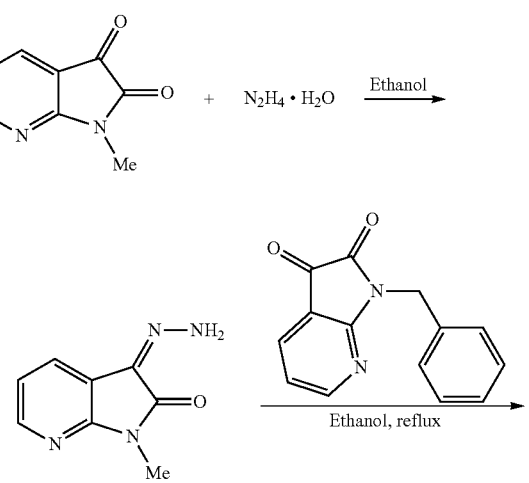

13

-continued

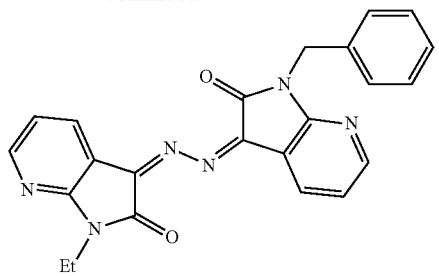

1.62 g (10 mmol) of 1-methyl-7-N isatin (1-methyl-pyrrolo[2,3-b]pyridine-2,3-dione) was dissolved in 50 mL of ethanol and placed in a flask. The 1-methyl-7-N isatin ethanol solution was slowly added to 50 mL ethanol solution containing 0.75 g (15 mmol) of hydrazine hydrate under stirring. The mixture was heated to 80° C. for 6 hours. After TLC indicated that reaction was completed, the hot reaction mixture was filtered, and washed with ethanol. The filtrate was cooled and filtered to obtain an intermediate. The resulting intermediate was placed in a reactor with 2.38 g (10 mmol) of 1-benzyl-7-N isatin (1-benzylpyrrolo[2,3-b]pyridine-2,3-dione), and 50 mL of ethanol was added to the reactor. The resulted mixture was heated to reflux at 80° C. under stirring for 6 hours. After TLC indicated that the reaction was completed, hearting was stopped and condensing device was removed. The reaction mixture was concentrated under reduced pressure, cooled to room temperature, and filtered. The filter cake was washed with warm water to obtain crude compound (4). Crude compound (4) was added to a reactor with 25 mL of ethanol for recrystallization. After filtration and drying, final product, sepia crystalline powder (2.51 g), was obtained with an overall yield of 63.5%.

(4)

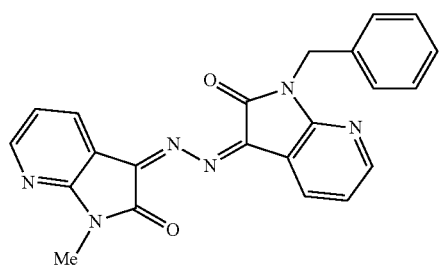

Compound (4) is sepia crystalline powder. M.P. 214.3° C.; $^1$H-NMR (400 MHz, DMSO-$d_6$) δ(ppm): 8.33, 8.31 (2H, m, J=7.5 Hz, 1.5 Hz), 7.96 (2H, d, J=7.5 Hz), 7.32-7.22 (5H, m, J=7.5 Hz), 6.88 (2H, t, J=7.5 Hz, 1.5 Hz), 4.79 (2H, s), 3.42 (3H, s); $^{13}$C-NMR (101 MHz, DMSO-$d_6$) δ(ppm): 163.7, 161.5, 160.9, 153.3, 145.8, 140.8, 138.7, 138.5, 138.2, 136.3, 128.7, 127.1, 126.9, 120.7, 113.6, 111.8, 49.6, 30.3; MS (ESI) for (M+H)$^+$: 397.1.

14

Example 5

The preparation of compound (5) (Z)-3-((Z)-(1-ethyl-2-oxo-1H-pyrrolo[2,3-b]pyridin-3(2H)-ylidene)hydrazono)-1-methyl-1H-pyrrolo[3,2-b]pyridin-2(3H)-one is shown below.

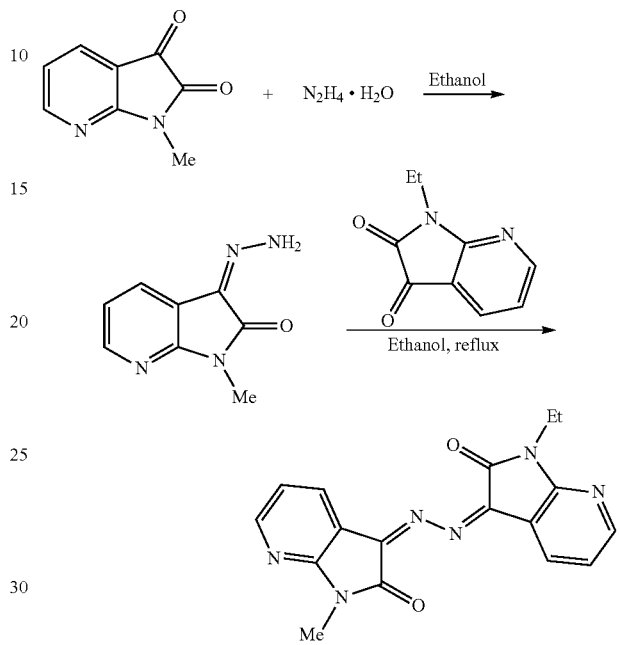

1.62 g (10 mmol) of 1-methyl-7-N isatin (1-methylpyrrolo[2,3-b]pyridine-2,3-dione) was dissolved in 50 mL of ethanol and placed in a flask. The 1-methyl-7-N isatin ethanol solution was slowly added to 50 mL ethanol solution containing 0.75 g (15 mmol) of hydrazine hydrate under stirring. The mixture was heated to 80° C. for 6 hours. After TLC indicated that reaction was completed, the hot reaction mixture was filtered, and washed with ethanol. The filtrate was cooled and filtered to obtain an intermediate. The resulting intermediate was placed in a reactor with 1.76 g (10 mmol) of 1-ethyl-7-N isatin (1-ethyl-pyrrolo[2,3-b]pyridine-2,3-dione), and 50 mL of ethanol was added to the reactor. The resulted mixture was heated to reflux at 80° C. under stirring for 6 hours. After TLC indicated that the reaction was completed, hearting was stopped and condensing device was removed. The reaction mixture was concentrated under reduced pressure, cooled to room temperature, and filtered. The filter cake was washed with warm water to obtain crude compound (5). Crude compound (5) was added to a reactor with 25 mL of ethanol for recrystallization. After filtration and drying, final product, white crystalline powder (1.18 g), was obtained with an overall yield of 35.2%.

(5)

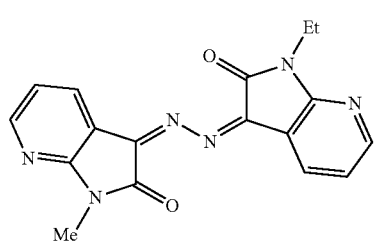

Compound (5) is white crystalline powder. M.P. 195.6° C.; ¹H-NMR (400 MHz, DMSO-d$_6$) δ(ppm): 8.33, 8.31 (2H, m, J=7.5 Hz, 1.5 Hz), 7.96 (2H, d, J=7.5 Hz), 6.88 (2H, t, J=7.5 Hz), 4.30 (2H, q), 3.42 (3H, s), 1.39 (3H, t); ¹³C-NMR (101 MHz, DMSO-d$_6$) δ(ppm): 163.7, 163.4, 161.8, 161.0, 153.3, 145.8, 140.7, 138.7, 138.5, 127.3, 120.7, 113.6, 111.8, 48.9, 30.3, 13.9; MS (ESI) for (M+H)⁺: 335.1.

Example 6

The preparation of compound (6) (Z)-1-ethyl-3-((Z)-(1-isopropyl-2-oxo-1H-pyrrolo[2,3-b]pyridin-3(2H)-ylidene) hydrazono)-1H-pyrrolo[3,2-b]pyridin-2(3H)-one is shown below.

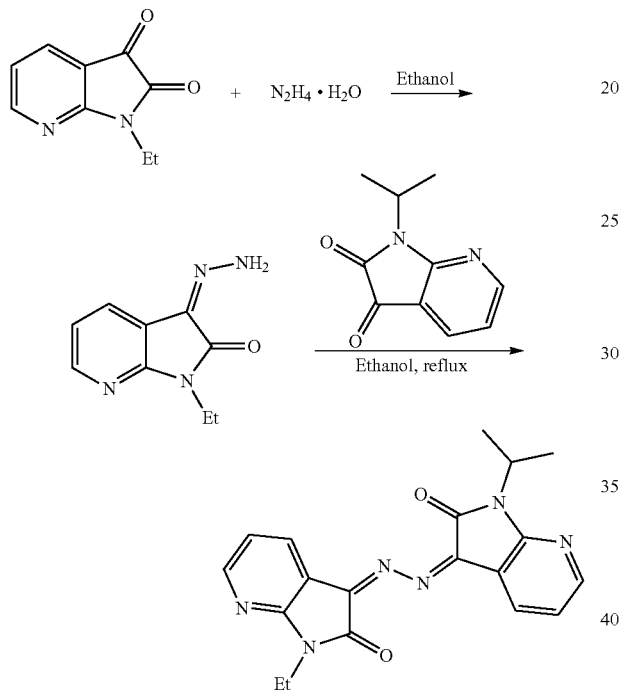

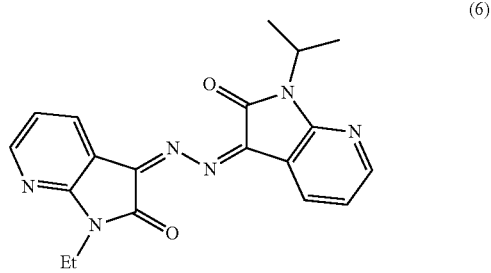 [SMILES: CCN1C(=O)/C(=N\N=C2/C(=O)N(C(C)C)c3ncccc32)c2cccnc21]

Compound (6) is red crystalline powder. M.P. 191.9° C.; ¹H-NMR (400 MHz, DMSO-d$_6$) δ(ppm): 8.33, 8.31 (2H, m, J=7.5 Hz), 7.96 (2H, d, J=1.5 Hz), 6.88 (2H, t, J=7.5 Hz), 4.30 (2H, q), 3.96 (1H, m), 1.40 (3H, t), 1.29 (6H, d, J=6.8 Hz); ¹³C-NMR (101 MHz, DMSO-d$_6$) δ (ppm): 163.4, 161.8, 160.9, 153.3, 145.7, 140.8, 138.5, 138.2, 127.4, 120.7, 113.6, 111.8, 58.6, 42.4, 20.8, 13.9; MS (ESI) for (M+H)⁺: 363.2.

Example 7

The preparation of compound (7) (Z)-3-((Z)-(1-isopropyl-2-oxo-1H-pyrrolo[2,3-b]pyridin-3(2H)-ylidene)hydrazono)-1-methyl-1H-pyrrolo[3,2-b]pyridin-2(3H)-one is shown below.

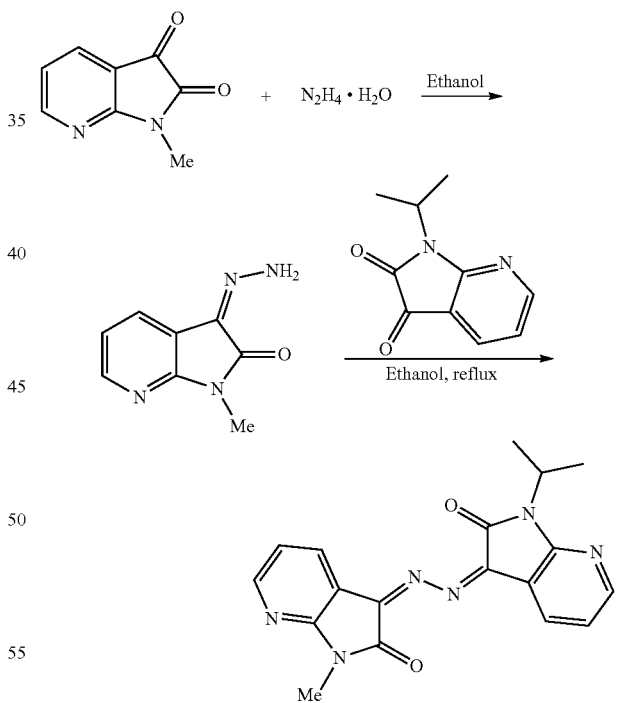

1.76 g (10 mmol) of 1-ethyl-7-N isatin (1-ethyl-pyrrolo[2,3-b]pyridine-2,3-dione) was dissolved in 50 mL of ethanol and placed in a flask. The 1-ethyl-7-N isatin ethanol solution was slowly added to 50 mL ethanol solution containing 0.75 g (15 mmol) of hydrazine hydrate under stirring. The mixture was heated to 80° C. for 6 hours. After TLC indicated that reaction was completed, the hot reaction mixture was filtered, and washed with ethanol. The filtrate was cooled and filtered to obtain an intermediate. The resulting intermediate was placed in a reactor with 1.90 g (10 mmol) of 1-isopropyl-7-N isatin (1-isopropyl-pyrrolo[2,3-b]pyridine-2,3-dione), and 50 mL of ethanol was added to the reactor. The resulted mixture was heated to reflux at 80° C. under stirring for 6 hours. After TLC indicated that the reaction was completed, hearting was stopped and condensing device was removed. The reaction mixture was concentrated under reduced pressure, cooled to room temperature, and filtered. The filter cake was washed with warm water to obtain crude compound (6). Crude compound (6) was added to a reactor with 25 mL of ethanol for recrystallization. After filtration and drying, final product, red crystalline powder (2.49 g), was obtained with an overall yield of 68.7%.

1.62 g (10 mmol) of 1-methyl-7-N isatin (1-methyl-pyrrolo[2,3-b]pyridine-2,3-dione) was dissolved in 50 mL of ethanol and placed in a flask. The 1-methyl-7-N isatin ethanol solution was slowly added to 50 mL ethanol solution containing 0.75 g (15 mmol) of hydrazine hydrate under stirring. The mixture was heated to 80° C. for 6 hours. After TLC indicated that reaction was completed, the hot reaction mixture was filtered, and washed with ethanol. The filtrate was cooled and filtered to obtain an intermediate. The resulting intermediate was placed in a reactor with 1.90 g (10 mmol) of 1-isopropyl-7-N isatin (1-isopropyl-pyrrolo[2,3-b]pyridine-2,3-dione), and 50 mL of ethanol was added to the reactor. The resulted mixture was heated to reflux at 80° C. under stirring for 6 hours. After TLC indicated that the reaction was completed, hearting was stopped and condensing device was removed. The reaction mixture was concentrated under reduced pressure, cooled to room temperature, and filtered. The filter cake was washed with warm water to obtain crude compound (7). Crude compound (7) was added to a reactor with 25 mL of ethanol for recrystallization. After filtration and drying, final product, red crystalline powder (1.90 g), was obtained with an overall yield of 54.5%.

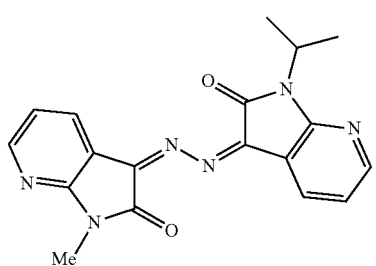

(7)

Compound (7) is red powder. M.P. 182.5° C.; $^1$H-NMR (400 MHz, DMSO-d$_6$) δ(ppm): 8.33, 8.31 (2H, m, J=7.5 Hz), 7.96 (2H, d, J=1.5 Hz), 6.88 (2H, t, J=7.5 Hz), 3.96 (1H, m), 3.42 (3H, s), 1.29 (6H, d, J=6.8 Hz); 13C-NMR (101 MHz, DMSO-d6) δ (ppm): 163.7, 163.1, 161.8, 161.0, 158.3, 145.8, 140.7, 138.6, 138.5, 127.3, 120.6, 113.5, 111.7, 58.6, 30.2, 20.8; MS (ESI) for (M+H)$^+$: 349.1.

Example 8

The preparation of compound (8) (Z)-6-chloro-3-((Z)-(5-chloro-1-methyl-2-oxo-1H-pyrrolo[2,3-b]pyridin-3(2H)-ylidene)hydrazono)-1-ethyl-1H-pyrrolo[3,2-b]pyridin-2(3H)-one is shown below.

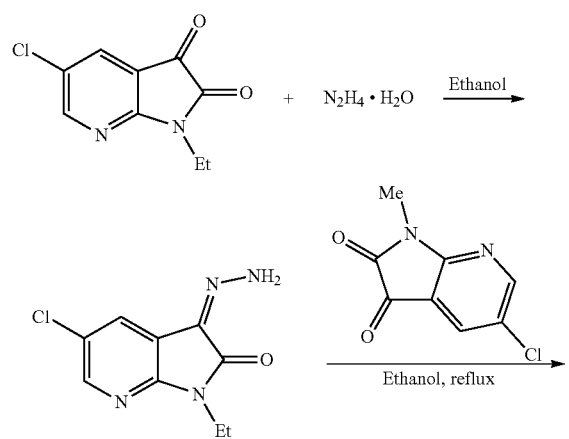

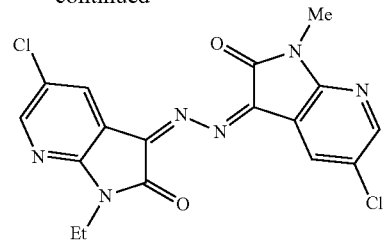

2.10 g (10 mmol) of 5-chloro-1-ethyl-7-N isatin (5-chloro-1-ethyl-pyrrolo[2,3-b]pyridine-2,3-dione) was dissolved in 50 mL of ethanol and placed in a flask. The 5-chloro-1-ethyl-7-N isatin ethanol solution was slowly added to 50 mL ethanol solution containing 0.75 g (15 mmol) of hydrazine hydrate under stirring. The mixture was heated to 80° C. for 6 hours. After TLC indicated that reaction was completed, the hot reaction mixture was filtered, and washed with ethanol. The filtrate was cooled and filtered to obtain an intermediate. The resulting intermediate was placed in a reactor with 1.96 g (10 mmol) of 5-chloro-1-methyl-7-N isatin (5-bromo-1-methyl-pyrrolo[2,3-b]pyridine-2,3-dione), and 50 mL of ethanol was added to the reactor. The resulted mixture was heated to reflux at 80° C. under stirring for 6 hours. After TLC indicated that the reaction was completed, hearting was stopped and condensing device was removed. The reaction mixture was concentrated under reduced pressure, cooled to room temperature, and filtered. The filter cake was washed with warm water to obtain crude compound (8). Crude compound (8) was added to a reactor with 25 mL of ethanol for recrystallization. After filtration and drying, final product, yellow crystalline powder (3.07 g), was obtained with an overall yield of 76.4%.

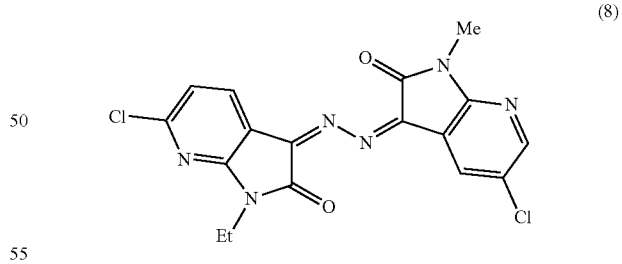

(8)

Compound (8) is yellow crystalline powder. M.P. 186.9° C.; $^1$H-NMR (400 MHz, DMSO-d$_6$) δ(ppm): 8.42 (1H, s, J=1.5 Hz), 8.34, 8.30 (2H, d, J=1.5 Hz), 7.76 (1H, d, J=1.5 Hz), 4.30 (2H, q), 3.42 (3H, s), 1.40 (3H, t); $^{13}$C-NMR (101 MHz, DMSO-d$_6$) δ (ppm): 163.7, 163.4, 160.9, 160.4, 153.1, 146.5, 141.0, 139.4, 138.5, 138.2, 137.4, 123.7, 118.6, 112.5, 42.4, 31.3, 13.9; MS (ESI) for (M+H)$^+$: 403.0.

Example 9

The preparation of compound (9) (Z)-6-bromo-3-((Z)-(5-chloro-1-ethyl-2-oxo-1H-pyrrolo[2,3-b]pyridin-3(2H)-ylidene)hydrazono)-1-methyl-1H-pyrrolo[3,2-b]pyridin-2(3H)-one is shown below.

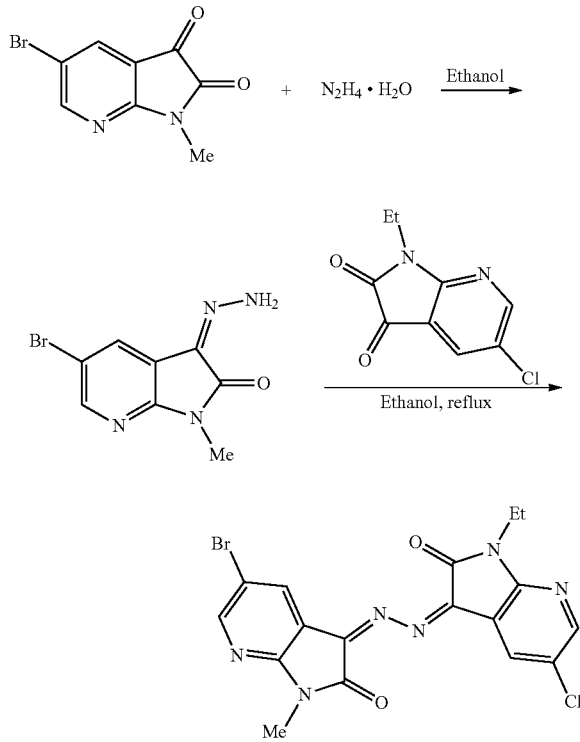

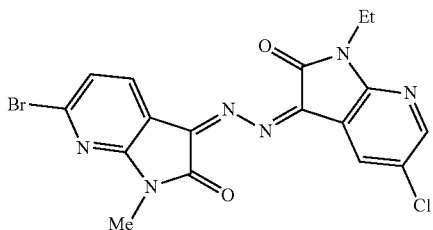

(9)

2.40 g (10 mmol) of 5-bromo-1-methyl-7-N isatin (5-bromo-1-methyl-pyrrolo[2,3-b]pyridine-2,3-dione) was dissolved in 50 mL of ethanol and placed in a flask. The 5-bromo-1-methyl-7-N isatin ethanol solution was slowly added to 50 mL ethanol solution containing 0.75 g (15 mmol) of hydrazine hydrate under stirring. The mixture was heated to 80° C. for 6 hours. After TLC indicated that reaction was completed, the hot reaction mixture was filtered, and washed with ethanol. The filtrate was cooled and filtered to obtain an intermediate. The resulting intermediate was placed in a reactor with 2.11 g (10 mmol) of 5-chloro-1-ethyl-7-N isatin (5-bromo-1-ethyl-pyrrolo[2,3-b]pyridine-2,3-dione), and 50 mL of ethanol was added to the reactor. The resulted mixture was heated to reflux at 80° C. under stirring for 6 hours. After TLC indicated that the reaction was completed, hearting was stopped and condensing device was removed. The reaction mixture was concentrated under reduced pressure, cooled to room temperature, and filtered. The filter cake was washed with warm water to obtain crude compound (9). Crude compound (9) was added to a reactor with 25 mL of ethanol for recrystallization. After filtration and drying, final product, reddish brown crystalline powder (3.54 g), was obtained with an overall yield of 79.3%.

Compound (9) is reddish brown crystalline powder. M.P. 205.2° C.; $^1$H-NMR (400 MHz, DMSO-d$_6$) δ(ppm): 8.42, 8.38 (2H, s, J=1.5 Hz), 8.20 (1H, d, J=1.5 Hz), 6.95 (1H, d, J=1.5 Hz), 4.31 (2H, q), 3.42 (3H, s), 1.30 (3H, t, J=8.0 Hz); 13C-NMR (101 MHz, DMSO-d$_6$) δ (ppm): 163.7, 161.0, 160.4, 153.1, 147.0, 143.3, 139.8, 138.5, 138.2, 123.7, 118.5, 118.4, 112.5, 48.8, 30.3, 13.9; MS (ESI) for (M+H)$^+$: 449.0.

Example 10

The preparation of compound (10) (Z)-3-((Z)-(1-benzyl-5-bromo-2-oxo-1H-pyrrolo[2,3-b]pyridin-3(2H)-ylidene)hydrazono)-6-chloro-1-ethyl-1H-pyrrolo[3,2-b]pyridin-2(3H)-one is shown below.

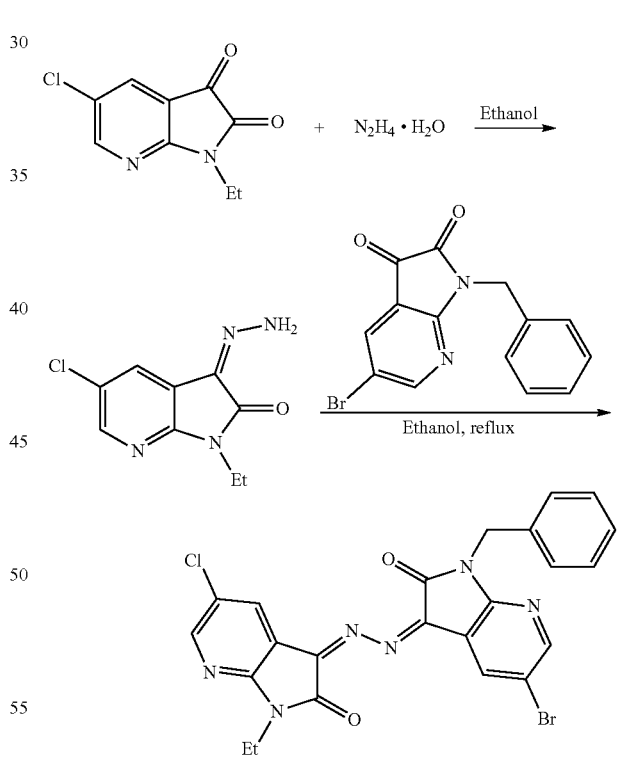

2.10 g (10 mmol) of 5-chloro-1-ethyl-7-N isatin (5-chloro-1-ethyl-pyrrolo[2,3-b]pyridine-2,3-dione) was dissolved in 50 mL of ethanol and placed in a flask. The 5-chloro-1-ethyl-7-N isatin ethanol solution was slowly added to 50 mL ethanol solution containing 0.75 g (15 mmol) of hydrazine hydrate under stirring. The mixture was heated to 80° C. for 6 hours. After TLC indicated that reaction was completed, the hot reaction mixture was filtered, and washed with ethanol. The filtrate was cooled and filtered to obtain an intermediate. The resulting intermediate was placed in a reactor with 3.16 g (10 mmol) of 5-bromo-1-benzyl-7-N isatin (5-bromo-1-benzyl-pyrrolo[2,3-b]pyridine-2,3-dione), and 50 mL of ethanol was added to the reactor. The resulted mixture was heated to reflux at 80° C. under stirring for 6 hours. After TLC indicated that the reaction was completed, hearting was stopped and condensing device was removed. The reaction mixture was concentrated under reduced pressure, cooled to room temperature, and filtered. The filter cake was washed with warm water to obtain crude compound (10). Crude compound (10) was added to a reactor with 25 mL of ethanol for recrystallization. After filtration and drying, final product, yellow brown crystalline powder (3.73 g), was obtained with an overall yield of 71.5%.

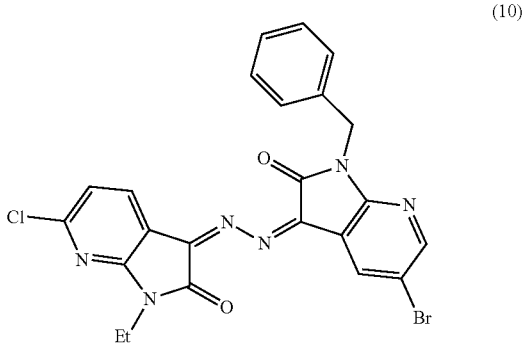 [SMILES: CCN1C(=O)/C(=N\N=C2/C(=O)N(Cc3ccccc3)c3ncc(Br)cc32)c2ccc(Cl)nc21]

(10)

Compound (10) is yellow brown crystalline powder. M.P. 233.8° C.; $^1$H-NMIR (400 MHz, DMSO-d$_6$) δ (ppm): 8.53 (1H, s, J=1.5 Hz), 8.33 (1H, d, J=1.5 Hz), 8.10 (1H, s, J=1.5 Hz), 7.32-7.22 (5H, m, J=7.5 Hz), 6.94 (1H, d, J=1.5 Hz), 4.79 (2H, s), 4.30 (2H, q), 1.39 (3H, t, J=8.0 Hz); 13C-NMR (101 MHz, DMSO-d6) δ (ppm): 163.7, 163.4, 160.9, 160.8, 155.4, 146.5, 141.6, 140.9, 139.4, 138.2, 137.5, 136.3, 128.7, 127.1, 126.9, 118.6, 113.0, 104.8, 49.6, 42.4, 13.9; MS (ESI) for (M+H)$^+$: 525.0.

Example 11

The preparation of compound (11) (Z)-6-chloro-3-((Z)-(1-ethyl-5-methyl-2-oxo-1H-pyrrolo[2,3-b]pyridin-3(2H)-ylidene)hydrazono)-1-methyl-1H-pyrrolo[3,2-b]pyridin-2(3H)-one is shown below.

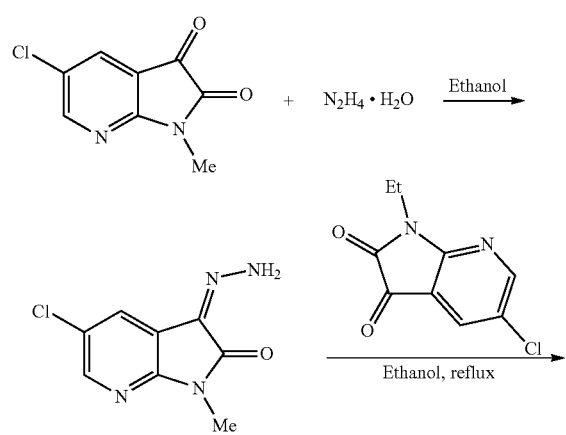

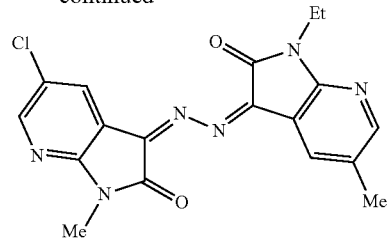

1.96 g (10 mmol) of 5-chloro-1-methyl-7-N isatin (5-chloro-1-methyl-pyrrolo[2,3-b]pyridine-2,3-dione) was dissolved in 50 mL of ethanol and placed in a flask. The 5-chloro-1-methyl-7-N isatin ethanol solution was slowly added to 50 mL ethanol solution containing 0.75 g (15 mmol) of hydrazine hydrate under stirring. The mixture was heated to 80° C. for 6 hours. After TLC indicated that reaction was completed, the hot reaction mixture was filtered, and washed with ethanol. The filtrate was cooled and filtered to obtain an intermediate. The resulting intermediate was placed in a reactor with 1.90 g (10 mmol) of 5-methyl-1-ethyl-7-N isatin (5-methyl-1-ethyl-pyrrolo[2,3-b]pyridine-2,3-dione), and 50 mL of ethanol was added to the reactor. The resulted mixture was heated to reflux at 80° C. under stirring for 6 hours. After TLC indicated that the reaction was completed, hearting was stopped and condensing device was removed. The reaction mixture was concentrated under reduced pressure, cooled to room temperature, and filtered. The filter cake was washed with warm water to obtain crude compound (11). Crude compound (11) was added to a reactor with 25 mL of ethanol for recrystallization. After filtration and drying, final product, yellow crystalline powder (2.67 g), was obtained with an overall yield of 69.8%.

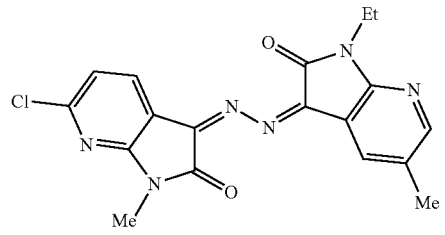

(11)

Compound (11) is yellow crystalline powder. M.P. 189.2° C.; $^1$H-NMR (400 MHz, DMSO-d$_6$) δ (ppm): 8.42 (1H, d, J=1.5 Hz), 8.12, 8.11 (2H, s, J=1.5 Hz), 7.26 (1H, d, J=1.5 Hz), 4.30 (2H, q), 3.42 (3H, s, J=7.5 Hz), 2.33 (3H, s, J=7.5 Hz), 1.40 (3H, t, J=8.0 Hz); $^{13}$C-NMR (101 MHz, DMSO-d$_6$) δ (ppm): 163.7, 162.5, 160.9, 159.5, 155.3, 146.5, 140.9, 139.4, 138.2, 137.5, 136.6, 119.3, 118.6, 111.0, 48.9, 30.3, 18.2, 13.9; MS (ESI) for (M+H)$^+$: 383.1.

Example 12

The Anti-Tumor Activity Test of the Compounds of The Present Invention

The compounds of the present invention were subjected to tumor cell proliferation inhibition test, and conventional MTT method was used.

Cell lines: human hepatoma cells (HepG2), human lung cancer cells (A-549), human gastric cancer cells (SGC-7901). The culture medium was DMEM+15% NBS+double antibody.

Sample solution preparation: after dissolving with DMSO (Merck), PBS (−) was added to obtain 100 μmol/L solution or homogeneous suspension. The solution was diluted with PBS (−) in DMSO to a final concentration of 0.1, 1, 10, 20, 40, 60, 80, 100 μmol/L.

Antitumor drug cytarabine (Ara-C) was used as control solution, prepared under the same condition.

Cell culture: adherent growth Tumor cells were cultured in 1640 medium containing 10% inactivated neonatal bovine serum and penicillin, streptomycin (1 million U/L), placed in carbon dioxide incubator at 37° C., 5% $CO_2$, and saturated humidity. Cells were treated serially passaged 2-3 times. The first culture was washed with PBS 2 times, and digested with trypsin. Fresh culture medium was added evenly, cells were adjusted to a appropriate concentration and transferred into a new culture flask. Cell in an exponential phase were chosen for the tests.

MTT Assay for Cell Viability and $IC_{50}$ Determination:

Experimental Principle: Living cells mitochondria in the dehydrogenase can reduce yellow MTT to water-insoluble blue-violet product MT (MTT formazan), deposited in the cells. The amount of production is proportional to the number of living cells. Dead cells do not reduce yellow MTT. DMSO can dissolve blue violet crystals, and the color depth is proportional to the amount contained, so the absorbance measured by the microplate reader can reflect the cell viability.

Methods: The exponential phase cells were digested and counted and seeded in 96-well plates at a density of 2×104/ mL at 100 μl per well. After 24 hours of incubation, the cells to be tested were treated with 0.1, 1, 10, 20, 40, 60, 80, 100 μmol/L of the compounds. Each experimental group had 5 wells in each concentration, and the culture medium containing 0.4% DMSO was used as control. After 48 hours, the supernatant was discarded, and 100 μl of MTT ((2-(4,5-dimethyl-2-thiazolyl)-3,5-diphenyl-2H-tetrazole hydrobromide) (1 mg/mL) was added to each well. After another 4 hours, the supernatant was discarded, and 100 μl of DMSO was added to each well. After mixing, the absorbance was measured at 570 nm using a microplate reader. An $IC_{50}$ calculation software was used to determine the half inhibitory concentration ($IC_{50}$).

The test results are shown in Table 1. The compounds listed in the table correspond to the compounds described above.

TABLE 1

Half Inhibitory Concentration of Compounds on Different Tumor Cells $IC_{50}$ (unit: μmol/L)

| Compounds | $IC_{50}$ (μmol/L) | | |
|---|---|---|---|
| | HepG2 | A549 | SGC-7901 |
| 1 | >100 | 55.78 ± 2.67 | 42.27 ± 1.89 |
| 2 | 9.31 ± 0.42 | 20.62 ± 0.55 | 19.39 ± 0.96 |
| 3 | 52.16 ± 1.77 | >100 | 33.68 ± 1.84 |
| 4 | >100 | 85.76 ± 2.96 | >100 |
| 5 | 28.69 ± 0.40 | 58. 24 ± 0.65 | 46.90 ± 0.85 |
| 6 | >100 | >100 | >100 |
| 7 | 98.58 ± 3.23 | >100 | >100 |
| 8 | >100 | >100 | 54.32 ± 2.85 |
| 9 | 22.36 ± 0.58 | 38.42 ± 0.79 | 39.99 ± 1.43 |
| 10 | 16.73 ± 0.45 | 26.61 ± 0.64 | 30.23 ± 1.01 |
| 11 | >100 | 68.47 ± 2.44 | >100 |
| Ara-C | 18.29 ± 0.28 | 14.92 ± 0.64 | 18.17 ± 0.39 |

The results show that compound (2) has excellent antitumor activities in the three cell lines tested. Compound (A-1) has the best antitumor activities. Compounds (10) and (9) also show good activities. The above experimental results indicates that the compounds of the present invention have good antitumor activities. Some compounds even have equal or better activities than Ara-C against certain cell lines. These compounds can be used for the study of antitumor research and drug development.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A compound with antitumor activities represented by formula I:

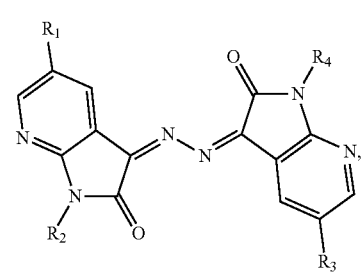

wherein $R_1$, $R_2$, $R_3$, and $R_4$ are independently hydrogen, nitro, alkoxy, halogen, unsubstituted or substituted phenyl, substituted or substituted benzyl, unsubstituted or substituted alkyl, or unsubstituted or substituted cycloalkyl.

2. The compound of claim 1, wherein $R_1$ is hydrogen, methoxy, nitro, halogen, unsubstituted or substituted alkyl, or unsubstituted or substituted cycloalkyl;

$R_2$ is hydrogen, unsubstituted or substituted alkyl, or unsubstituted or substituted cycloalkyl;

$R_3$ is hydrogen, methoxy, nitro, halogen, unsubstituted or substituted phenyl, or unsubstituted or substituted alkyl or cycloalkyl; and $R_4$ is hydrogen, methyl, unsubstituted or substituted phenyl, unsubstituted or substituted benzyl, unsubstituted or substituted alkyl, or unsubstituted or substituted cycloalkyl.

3. The compound of claim 1, wherein the compound is selected from the group consisting of:

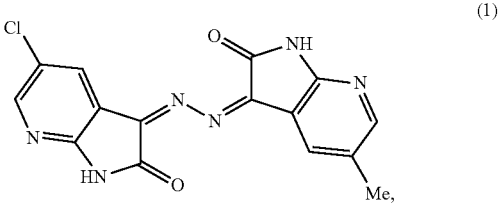

-continued
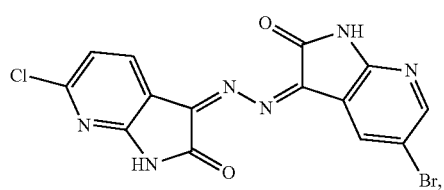
(2)
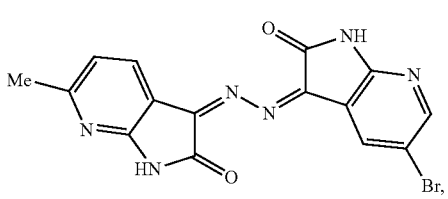
(3)
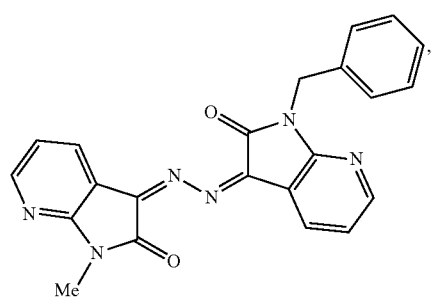
(4)
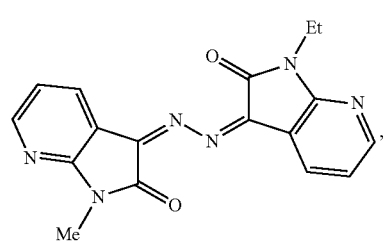
(5)
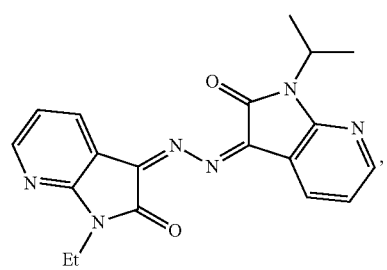
(6)
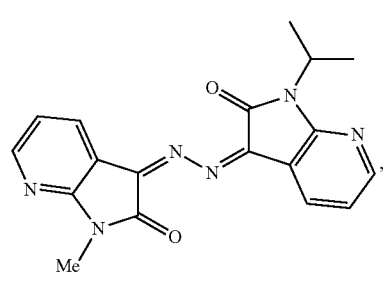
(7)
-continued
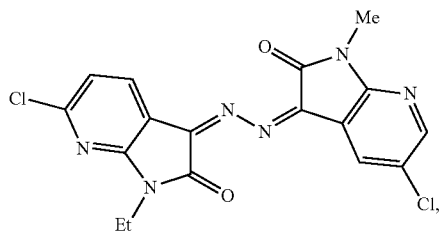
(8)
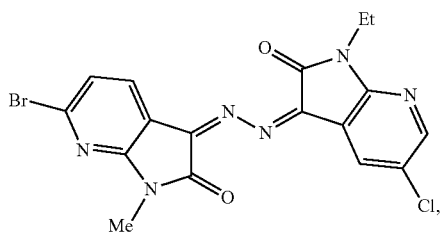
(9)
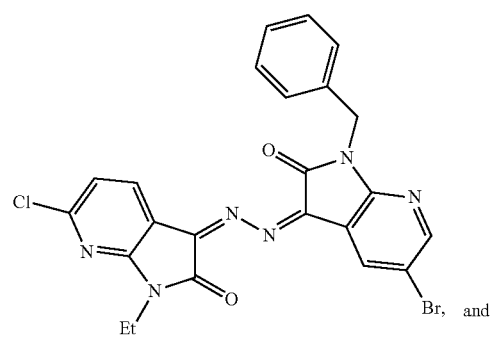
(10)
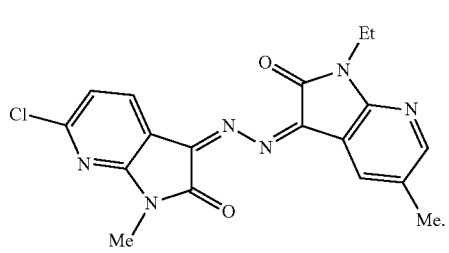
(11)
4. A method of preparing the compound of claim 1, comprising:
reacting a compound of formula II with hydrazine hydrate ($N_2H_4 \cdot H_2O$) in an organic solvent to obtain a compound of formula III, and
reacting the compound of formula III with a compound of formula IV in the organic solvent to obtain the compound of formula I,
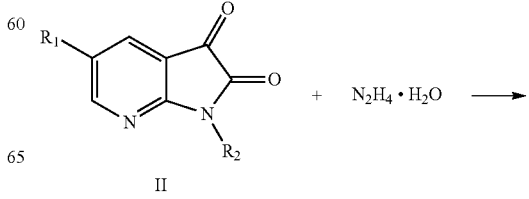
II

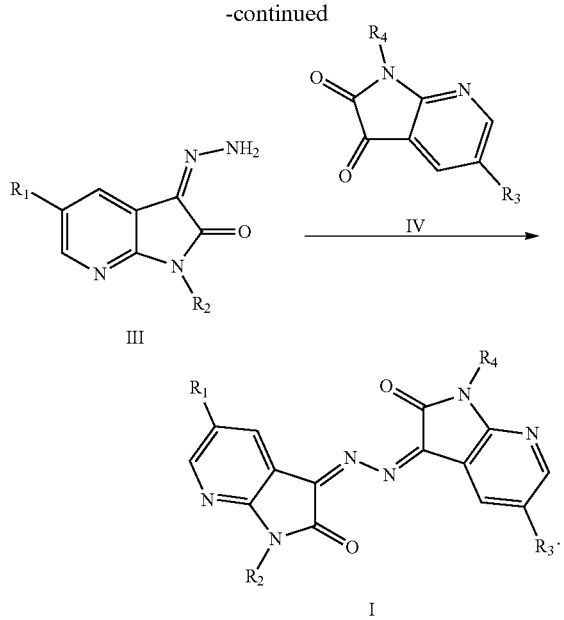

5. The method of claim 4, wherein the organic solvent is methanol, ethanol, or isopropanol.

6. The method of claim 4, wherein the compound of formula II and hydrazine hydrate ($N_2H_4 \cdot H_2O$) are heated in the organic solvent to 60-100° C. for 4 to 9 hours.

7. The method of claim 4, wherein the compound of formula III and the compound of formula IV are heated in the organic solvent to 60-100° C. for 2 to 6 hours.

8. The method of claim 4, further comprising:
    recrystallizing the compound of formula I in methanol, ethanol, or isopropanol.

9. The method of claim 4, wherein a molar ratio of the compound of formula II and hydrazine hydrate ($N_2H_4 \cdot H_2O$) is 1:1 to 1:2.5.

10. The method of claim 9, wherein the molar ratio of the compound of formula II and hydrazine hydrate ($N_2H_4 \cdot H_2O$) is 1:1.5 to 1:2.

11. The method of claim 4, wherein a molar ratio of the compound of formula III and the compound of formula IV is 1:1 to 1:1.5.

* * * * *